US00PP36798P2

(12) United States Plant Patent
Boyle

(10) Patent No.: US PP36,798 P2
(45) Date of Patent: Jul. 1, 2025

(54) ***AGERATUM* PLANT NAMED 'Agerboyuma'**

(50) Latin Name: *Ageratum houstonianum*
Varietal Denomination: Agerboyuma

(71) Applicant: Nancy S. Bandman, Hadley, MA (US)

(72) Inventor: Thomas H. Boyle, Hadley, MA (US)

(73) Assignees: The Estate of Thomas H. Boyce, Hadley, MA (US); University of Massachusetts, Boston, MA (US)

( * ) Notice: Subject to any disclaimer, the term of this patent is extended or adjusted under 35 U.S.C. 154(b) by 0 days.

(21) Appl. No.: 18/917,732

(22) Filed: Oct. 16, 2024

(51) Int. Cl.
*A01H 5/02* (2018.01)
*A01H 6/14* (2018.01)

(52) U.S. Cl.
USPC ..... Plt./400

(58) Field of Classification Search
USPC ..... Plt./263.1, 400
See application file for complete search history.

(56) References Cited

U.S. PATENT DOCUMENTS

PP18,186 P2 * 11/2007 Sanders ..... A01H 6/14
Plt./400

* cited by examiner

*Primary Examiner* — Karen M Redden
(74) *Attorney, Agent, or Firm* — C. Anne Whealy

(57) ABSTRACT

A new and distinct cultivar of *Ageratum* plant named 'Agerboyuma', characterized by its relatively compact, upright to outwardly spreading and mounding plant habit; moderately vigorous to vigorous growth habit; freely branching habit; relatively large leaves; freely and continuous flowering habit; light violet-colored inflorescences that resist fading; and good garden performance.

2 Drawing Sheets

Figure 1:
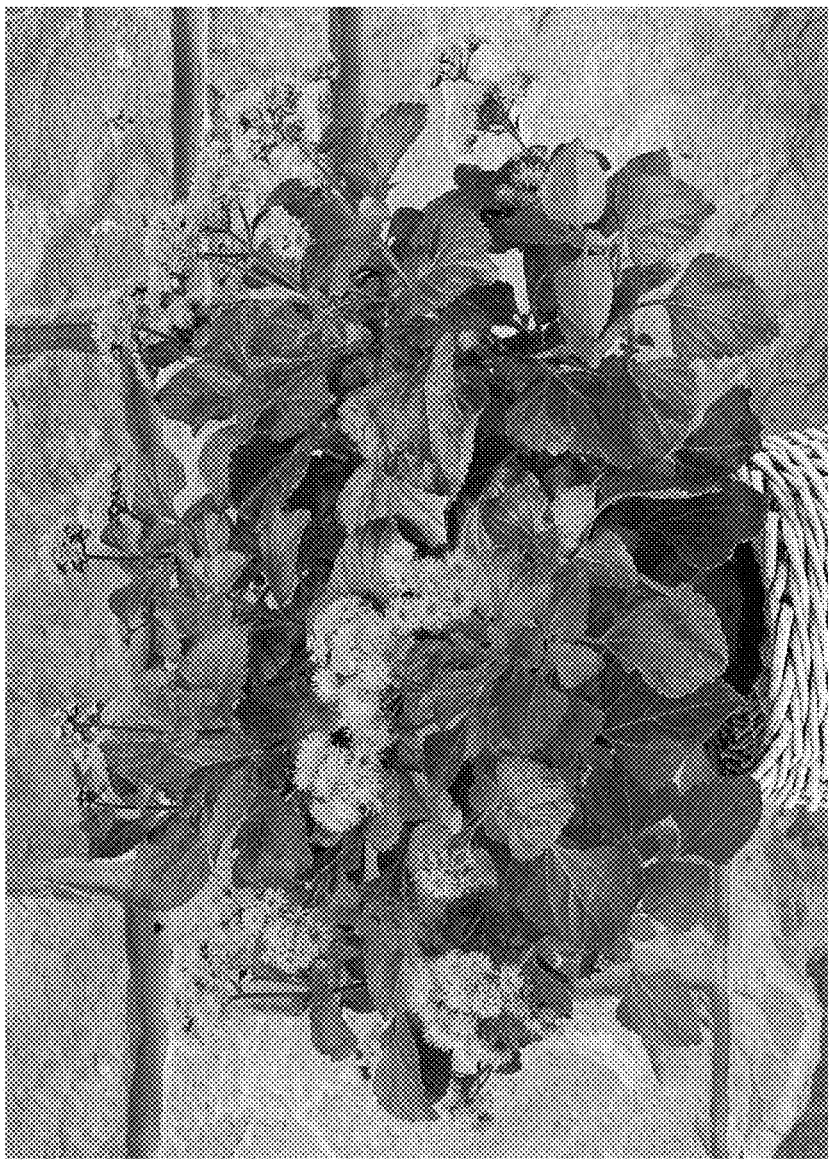

Botanical designation: *Ageratum houstonianum.*
Cultivar denomination: 'AGERBOYUMA'.

BACKGROUND OF THE INVENTION

The present invention relates to a new and distinct cultivar of *Ageratum* plant, botanically known as *Ageratum houstonianum*, commonly referred to as Floss Flower and hereinafter referred to by the name 'Agerboyuma'.

The new *Ageratum* plant is a product of a planned breeding program conducted by the Inventor in Amherst, Massachusetts. The objective of the breeding program was to create new *Ageratum* plants with a vigorous and uniform growth habit, strong and large leaves, numerous inflorescences and attractive inflorescence coloration.

The new *Ageratum* plant originated from a cross-pollination made by the Inventor in 2004 of *Ageratum houstonianum* 'Blue Danube', not patented, as the female, or seed, parent with *Ageratum houstonianum* 'Tulum', not patented, as the male, or pollen, parent. The new *Ageratum* plant was discovered and selected by the Inventor as a single flowering plant with the progeny of the stated cross-pollination grown in a controlled greenhouse environment in Amherst, Massachusetts in 2006.

Asexual reproduction of the *Ageratum* plant by vegetative cuttings in Amherst, Massachusetts since 2006, has shown that the unique features of this new *Ageratum* plant are stable and reproduced true to type in successive generations.

SUMMARY OF THE INVENTION

Plants of the new *Ageratum* have not been observed under all possible combinations of cultural and environmental conditions. The phenotype may vary somewhat with variations in environment such as temperature and light intensity without, however, any variance in genotype.

The following traits have been repeatedly observed and are determined to be the unique characteristics of 'Agerboyuma'. These characteristics in combination distinguish 'Agerboyuma' as a new and distinct cultivar of *Ageratum:*

1. Relatively compact, upright to outwardly spreading and mounding plant habit.
2. Moderately vigorous to vigorous growth habit.
3. Freely branching habit.
4. Relatively large leaves.
5. Freely and continuous flowering habit.
6. Light violet-colored inflorescences that resist fading.
7. Good garden performance.

Plants of the new *Ageratum* differ from plants of the parents, 'Blue Danube' and 'Tulum', primarily in plant habit as plants of the new *Ageratum* are more uniformly mounded than plants of the parent cultivars. In addition, plants of the new *Ageratum* have larger leaves than plants of the parent cultivars.

Plants of the new *Ageratum* can be compared to plants of *Ageratum* 'Agsantis', disclosed in U.S. Plant Pat. No. 15,289. In side-by-side comparisons, plants of the new *Ageratum* differ from plants of 'Agsantis' in the following characteristics:

1. Plants of the new *Ageratum* are more outwardly spreading than plants of 'Agsantis'.
2. Plants of the new *Ageratum* are more vigorous than plants of 'Agsantis'.
3. Plants of the new *Ageratum* have larger leaves than plants of 'Agsantis'.
4. Plants of the new *Ageratum* flower later than plants of 'Agsantis'.

5. Inflorescences of plants of the new *Ageratum* are light violet in color whereas inflorescences of plants of 'Agsantis' are light purple in color.

BRIEF DESCRIPTION OF THE PHOTOGRAPHS

The accompanying colored photographs illustrate the overall appearance of the new *Ageratum* plant, showing the colors as true as it is reasonably possible to obtain in colored reproductions of this type. Colors in the photographs may differ slightly from the color values cited in the detailed botanical description which accurately describe the actual colors of the new *Ageratum* plant.

The photograph on the first sheet (FIG. 1) is a side perspective view of a typical flowering plant of 'Agerboyuma' grown in a container.

Figure 2:
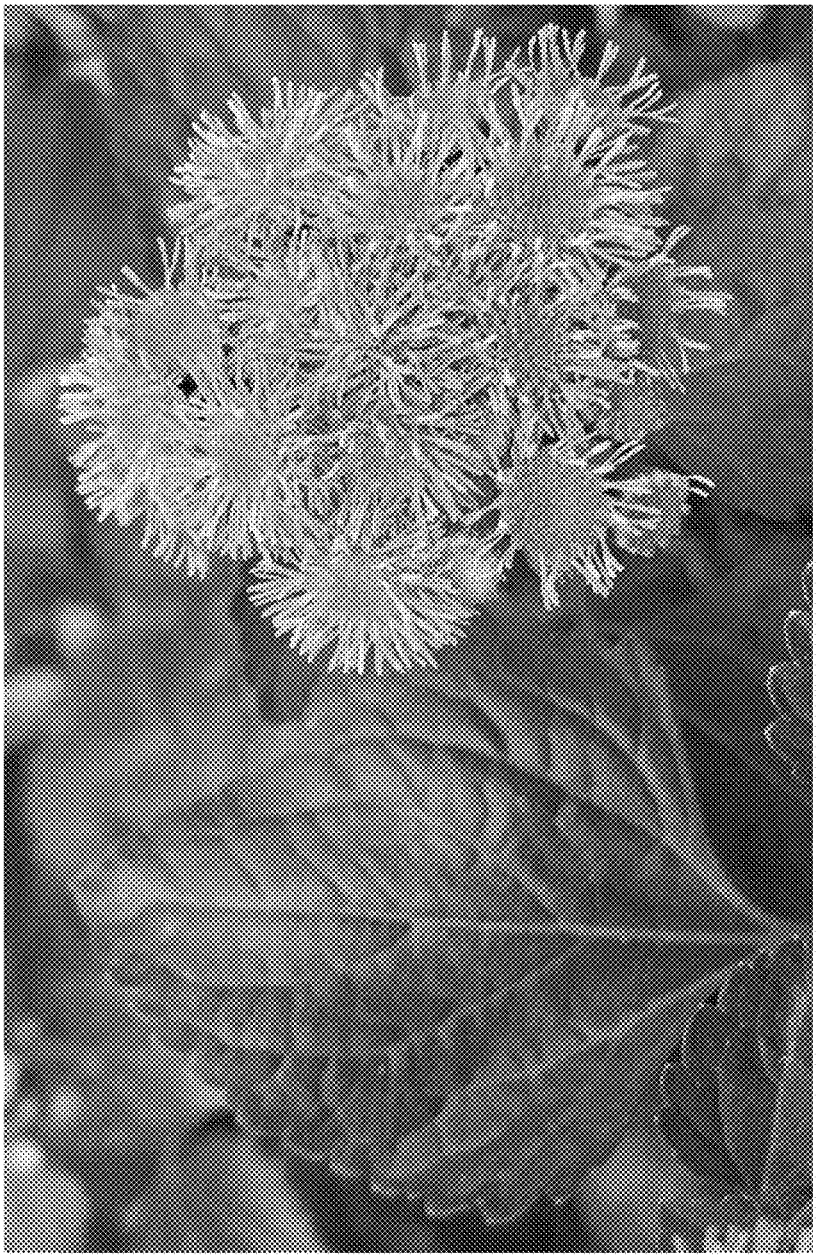

The photograph on the second sheet (FIG. 2) is a close-up view of a typical flowering plant of 'Agerboyuma'.

DETAILED BOTANICAL DESCRIPTION

Plants used for the aforementioned photographs and following description were grown under conditions which closely approximate commercial *Ageratum* production conditions during the winter in 11.5-cm containers in a polycarbonate-covered greenhouse in West Chicago, Illinois. During the production of the plants, day temperatures ranged from 16° C. to 24° C. and night temperatures ranged from 15° C. to 16° C. Plants were pinched one time and were 14 weeks old when the photographs and description were taken. In the following description, color references are made to The Royal Horticultural Society Colour Chart, 2015 Edition, except where general terms of ordinary dictionary significance are used.

Botanical classification: *Ageratum houstonianum* 'Agerboyuma'.

Parentage:

*Female, or seed, parent.*—*Ageratum houstonianum* 'Blue Danube', not patented.

*Male, or pollen, parent.*—*Ageratum houstonianum* 'Tulum', not patented.

Propagation:

*Type cutting.*—Vegetative terminal stem cuttings.

*Root description.*—Fine to medium in thickness, fibrous; typically whitish in color, however actual color of the roots is dependent on substrate composition, water quality, fertilizer, substrate temperature and physiological age of roots.

*Time to produce a rooted young plant, winter.*—About three weeks.

*Rooting habit.*—Freely branching; medium in density.

Plant description:

*Form.*—Relatively compact, upright to outwardly spreading and mounding plant habit; overall plant shape, broad inverted triangle; freely branching habit with about four to five primary lateral branches each primary lateral branch with secondary lateral branches potentially developing at every node; pinching enhances lateral branch development; moderately vigorous to vigorous growth habit.

*Plant height.*—About 20 cm to 23 cm.

*Plant width.*—About 35 cm by 41 cm.

*Lateral branch description.*—Length: About 24 cm to 28 cm. Diameter: About 5 mm. Internode length: About 2.2 cm to 2.5 cm. Strength: Strong; when developing, flexible and becoming less flexible with subsequent development. Texture and luster: Very fine pubescence; slightly glossy. Color, developing: Close to 144A. Color, developed: Close to 146A.

Foliage description:

*Arrangement.*—Opposite, simple.

*Length.*—About 5.2 cm to 5.7 cm.

*Width.*—About 5.1 cm to 5.5 cm.

*Shape.*—Deltoid.

*Apex.*—Acute.

*Base.*—Broadly cuneate with truncate tendencies.

*Margin.*—Crenate.

*Texture and luster, upper and lower surfaces.*—Smooth, glabrous; slightly glossy.

*Venation pattern.*—Pinnate, arcuate.

*Color.*—Developing leaves, upper surface: Close to 146A. Developing leaves, lower surface: Close to 146B. Fully expanded leaves, upper surface: Close to 147A; venation, close to 146B. Fully expanded leaves, lower surface: Close to 146A to 146B; venation, close to 148C.

*Petioles.*—Length: About 2.2 cm to 3.5 cm. Diameter: About 3 mm to 4 mm. Strength: Strong, flexible. Texture and luster, upper and lower surfaces: Smooth, glabrous; slightly glossy. Color, upper surface: Close to 146A. Color, lower surface: Close to 146B.

Inflorescence description:

*Inflorescence arrangement, form and habit.*—Individual rotate composite-type inflorescences arranged in rounded terminal and axillary compound corymbs; freely flowering habit with about 16to 22 inflorescences per corymb; inflorescences face mostly upright to slightly outwardly; elongated linear ray florets and tubular disc florets arranged acropetally on the receptacle; ray and disc floret colors do not fade with development.

*Natural flowering season.*—Under greenhouse conditions and dependent on temperature, plants begin flowering about eight to nine weeks after planting rooted cuttings; in the garden, plants will flower continuously from spring until frost.

*Inflorescence longevity on the plant.*—Under outdoor conditions and dependent on temperature, individual inflorescences typically last about seven to ten days on the plant; inflorescences persistent.

*Fragrance.*—Faintly fragrant; pleasant.

*Inflorescence buds.*—Length: About 4 mm. Diameter: About 5 mm. Shape: Ovoid. Texture and luster: Smooth, glabrous; slightly glossy. Color: Close to 146A.

*Corymb diameter.*—About 4 cm by 5.5 cm.

*Corymb height.*—About 2.2 cm to 2.5 cm.

*Individual inflorescence diameter.*—About 1.1 cm by 1.5 cm.

*Individual inflorescence height.*—About 1.1 cm.

*Receptacle diameter.*—About 4 mm.

*Receptacle height.*—About 4 mm.

*Receptacle color.*—Close to 144A.

*Ray florets.*—Quantity per inflorescence: About 20 to 30 arranged in a single whorl exterior to the disc florets. Length: About 3.5 mm to 5 mm. Width: About 1 mm to 1.5 mm. Shape: Elongated linear, almost threadlike. Apex: Acute or emarginate. Base: Attenuate; fused at the base into a short tube. Margin: Entire. Aspect: Mostly flat to slightly twisting.

Texture and luster, upper and lower surfaces: Smooth, glabrous; matte. Color: When opening and fully opened, upper surface: Close to 91A; towards the base, close to NN155D and at the base, close to 144A. When opening and fully opened, lower surface: Close to 91A to 91B; towards the base, close to NN155D and at the base, close to 144A.

*Disc florets*.—Quantity per inflorescence: About 50 to 70 in numerous spiral whorls at the center of the inflorescence. Length: About 2 mm. Width: About 1 mm. Shape: Tubular, narrow, fused. Apex: Acute, five-pointed. Margin: Entire. Texture and luster, inner and outer surfaces: Smooth, glabrous; matte. Color, immature and mature, inner and outer surfaces: Apex: Close to 91A. Mid-section: Close to NN155D. Base: Close to 144A.

*Involucral bracts* (*phyllaries*).—Quantity per inflorescence: About 18 to 24, imbricate and arranged in about two whorls. Length: About 3.5 mm to 4 mm. Width: About 1 mm. Shape: Ligulate. Apex: Acute. Base: Truncate, fused at the base of the receptacle. Margin: Entire. Texture and luster, upper and lower surfaces: Smooth, glabrous; slightly glossy. Color, upper surface: Close to 144A. Color, lower surface: Close to between 144A and 146A.

*Peduncles*.—Length: About 9 mm to 11 mm. Diameter: About 1 mm to 2 mm. Angle: Mostly upright to 45° from vertical. Strength: Strong, wiry. Texture and luster: Smooth, glabrous; slightly glossy. Color: Close to between 144A and 146A.

*Reproductive organs* (*present on disc florets only*).—Androecium: Filament length: About 1 mm to 1.5 mm. Filament color: Close to 157D. Anthers: None observed. Gynoecium: Quantity per floret: One. Pistil length: About 6 mm to 7 mm. Stigma shape: Threadlike, bi-parted. Stigma color: Close to 91A. Style length: About 5 mm. Style color: Close to 144A. Ovary color: Close to 144A.

*Seeds and fruit*.—To date, seed and fruit production have not been observed.

Pathogen & pest resistance: To date, plants of the new *Ageratum* have not been noted to be resistant to pathogens and pests common to *Ageratum* plants.

Garden performance: Plants of the new *Ageratum* have been observed to have good garden performance and to tolerate rain, wind and temperatures ranging from about 2° C. to about 45° C.

It is claimed:

1. A new and distinct *Ageratum* plant named 'Agerboyuma' as herein illustrated and described.

* * * * *